(12) United States Patent
Miglietti et al.

(10) Patent No.: US 11,413,178 B2
(45) Date of Patent: Aug. 16, 2022

(54) INTRAGASTRIC BALLOON AND MANUFACTURING METHOD THEREOF

(71) Applicant: EUROMEDICAL S.R.L., San Zeno Naviglio (IT)

(72) Inventors: Romano Miglietti, San Zeno Naviglio (IT); Giorgio Ramorino, San Zeno Naviglio (IT); Matteo Storer, San Zeno Naviglio (IT)

(73) Assignee: EUROMEDICAL S.R.L., San Zeno Naviglio (IT)

( * ) Notice: Subject to any disclaimer, the term of this patent is extended or adjusted under 35 U.S.C. 154(b) by 465 days.

(21) Appl. No.: 16/324,326

(22) PCT Filed: Aug. 10, 2017

(86) PCT No.: PCT/IB2017/054879
§ 371 (c)(1),
(2) Date: Feb. 8, 2019

(87) PCT Pub. No.: WO2018/029625
PCT Pub. Date: Feb. 15, 2018

(65) Prior Publication Data
US 2020/0352766 A1    Nov. 12, 2020

(30) Foreign Application Priority Data
Aug. 10, 2016  (IT) .................. 102016000084458

(51) Int. Cl.
*A61F 5/00* (2006.01)
(52) U.S. Cl.
CPC ............ *A61F 5/0036* (2013.01); *A61F 5/003* (2013.01)

(58) Field of Classification Search
CPC .... A61F 5/0036; A61F 5/0013; A61F 5/0076; A61F 5/004; A61F 5/0043; A61F 5/0046;
(Continued)

(56) References Cited

U.S. PATENT DOCUMENTS 1,878,715 A * 9/1932 Saul ...................... F16K 15/202
                                                       473/610
4,287,920 A * 9/1981 Johnson, Jr. .............. A61F 5/34
                                                       141/313
(Continued)

FOREIGN PATENT DOCUMENTS

DE    3310234 A1    9/1984
EP    1929957 A1    6/2008

OTHER PUBLICATIONS

International Search Report and Written Opinion for International Application No. PCT/IB2017/054879 dated Dec. 1, 2017.

*Primary Examiner* — Tan-Uyen T Ho
*Assistant Examiner* — Bridget E. Rabaglia
(74) *Attorney, Agent, or Firm* — Lando & Anastasi, LLP

(57) ABSTRACT

An intragastric balloon comprises a bag body, provided with an internal cavity shaped to contain a filling fluid, and a valve having a valve body provided with a through inner conduit for feeding the filling fluid into the cavity; the valve body is flexible and elastically deformable, being made of an elastic material; and is arranged inside the bag body and shaped so as to elastically deform until it occludes the conduit following a pressure exerted on an outer surface of the valve body by the filling fluid contained in the cavity.

14 Claims, 4 Drawing Sheets

(58) Field of Classification Search
CPC ............. A61F 5/003; A61M 25/10181; A61M 25/10185; A61M 2025/1054; A61M 2039/064; A61B 17/12136; A61B 2017/12081; B60C 29/00; A63H 2027/1083; Y10S 2/03
USPC ........................................................ 606/192
See application file for complete search history.

(56) References Cited

U.S. PATENT DOCUMENTS

| | | | |
|---|---|---|---|
| 4,739,758 A | | 4/1988 | Lai et al. |
| 5,127,627 A | * | 7/1992 | Wiser .................... F16K 15/202 251/149.1 |
| 7,854,028 B1 | * | 12/2010 | Williams ............... A47K 13/14 4/245.6 |
| 2002/0055757 A1 | * | 5/2002 | Torre ....................... A61F 5/003 606/192 |
| 2006/0142700 A1 | * | 6/2006 | Sobelman ............. A61F 5/0036 604/167.04 |
| 2008/0097509 A1 | * | 4/2008 | Beyar ................ A61B 17/0057 606/192 |
| 2017/0292511 A1 | * | 10/2017 | Frayne .................... F04B 33/00 |
| 2020/0345528 A1 | * | 11/2020 | Shi .......................... A61F 5/003 |

\* cited by examiner

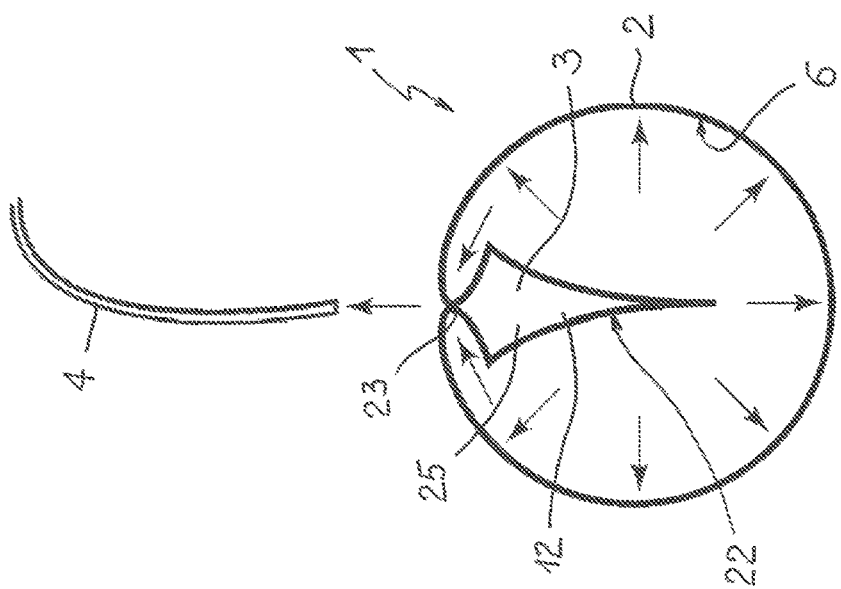
Fig. 3
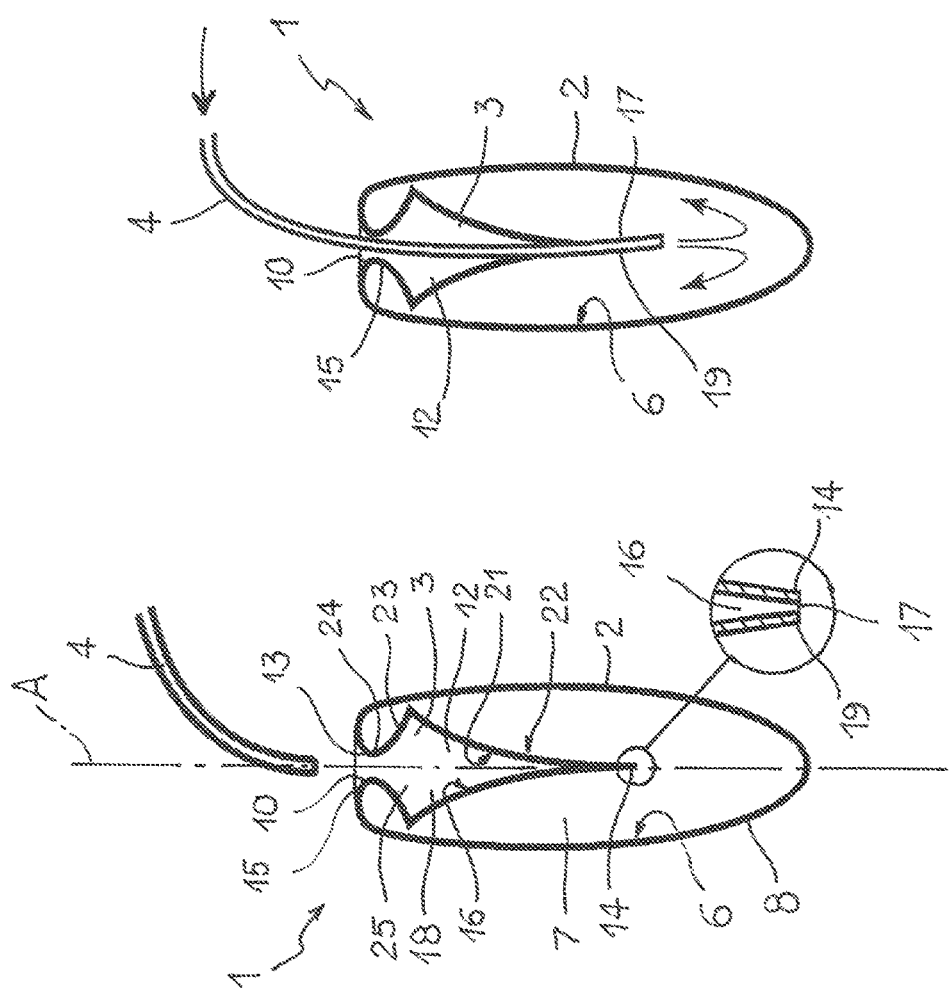
Fig. 2
Fig. 1

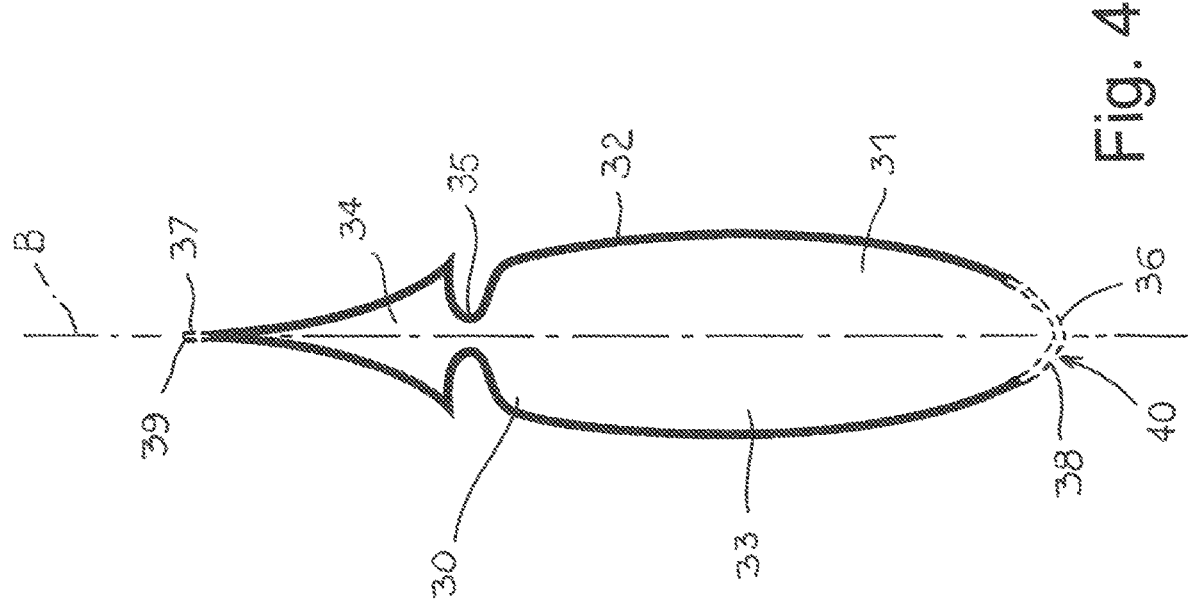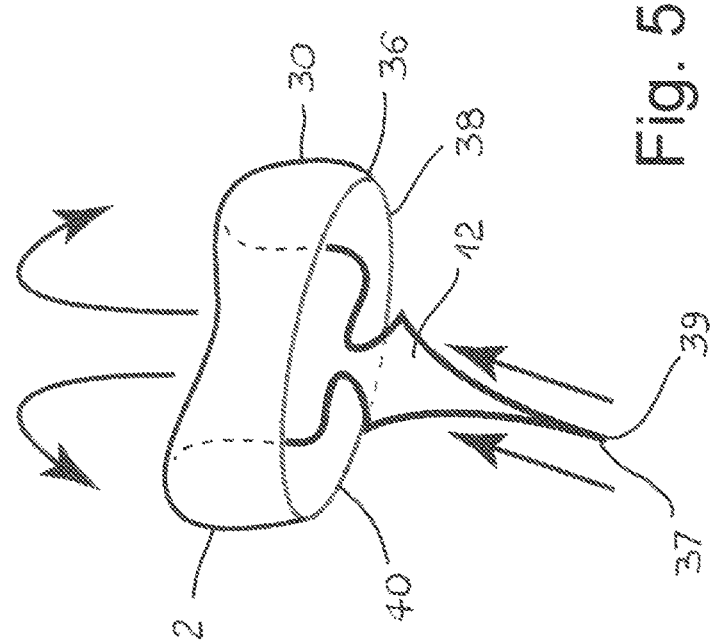

INTRAGASTRIC BALLOON AND MANUFACTURING METHOD THEREOF

CROSS REFERENCE TO RELATED APPLICATIONS

This application is a U.S. National Stage Application under 35 U.S.C. § 371 of International Application No. PCT/IB2017/054879, filed Aug. 10, 2017, which claims priority under IT102016000084458, filed on Aug. 10, 2016. The entire contents of each of the foregoing applications are incorporated herein by reference.

TECHNICAL FIELD

The present invention concerns an intragastric balloon, which can be used for example in the treatment of obesity, and manufacturing method thereof.

BACKGROUND ART

As is known, a technique for treating obesity entails the insertion of an intragastric balloon to reduce the dimensions of the stomach and consequently its capacity to store food.

In general, an intragastric balloon consists of an expandable bag made of elastic material, for example polyurethane or latex, provided with a valve that allows the filling thereof with an appropriate filling fluid, for example water or saline solution (if necessary with a dye that highlights any leaks) or a gas (air or inert gas).

The intragastric balloon is introduced into the empty stomach and then filled, through the valve, with the filling fluid which expands the balloon to the desired dimension.

The balloon is normally positioned by means of trans-oral procedure (i.e. through the oral channel), without requiring surgery.

The balloon is also removed through the oral channel, after the balloon has been deflated by emptying the filling fluid directly into the stomach. The filling fluid is discharged for example through holes made in the balloon with a gastroscopic instrument.

The main drawback associated with the use of intragastric balloons is connected with the mode of insertion through the oral channel.

In the majority of cases, the intragastric balloon is inserted into the stomach of a patient by means of a probe which pushes the deflated balloon into the oral channel, via the esophagus; in the oral channel a gastroscope is present (at least during some phases of insertion of the balloon by means of the probe), necessary for the doctor to see inside the stomach.

The patient therefore feels great discomfort, due to the overall dimensions of the probe which pushes the balloon together with the adjacent gastroscope.

In order to remedy this drawback, the patent application BS2015A000003 describes an intragastric balloon with a reduced thickness, such that the balloon, when deflated, can be folded over and/or coiled around itself until reaching a cross section dimension of less than 3.8 mm, so that it can be inserted into the stomach of a patient through the operating channel of a standard gastroscope.

However, the valve with which the balloon is necessarily provided also contributes to the overall dimensions of the deflated and folded/coiled balloon.

In the known balloons, the valve normally consists of a separate component which is mounted and fixed on the balloon. In general, the valve, however small, has a non-negligible overall dimension. The valve, therefore, in addition to requiring specific production and assembly operations (which obviously affect the cost and complexity of the balloon as a whole), also poses a limit in terms of overall dimension which is difficult to overcome with the components and materials used in the known art.

Examples of intragastric balloons with valves manufactured separately and then applied to the balloons are described in U.S. Pat. No. 4,739,758A, DE3310234A1, EP1929957A1.

In short, the intragastric balloons of the known art are not fully satisfactory, either in terms of overall dimension and therefore ease of use, or in terms of simplicity of production.

DISCLOSURE OF INVENTION

One object of the present invention is to provide an intragastric balloon which is free from the drawbacks of the known art highlighted here; in particular, one object of the invention is to provide an intragastric balloon that can be inserted into the stomach with minimum discomfort for the patient, for example using a standard gastroscope.

A further object of the invention is to provide an intragastric balloon that is both extremely simple and relatively inexpensive to produce, and can be manufactured by means of a simple inexpensive manufacturing method.

According to said objects, the present invention concerns an intragastric balloon and manufacturing method thereof as defined in essential terms in the attached claims 1 and 14 respectively, with the preferred additional characteristics described in the dependent claims.

The intragastric balloon of the invention is extremely simple and relatively inexpensive to produce and can be inserted in the stomach with minimum discomfort for the patient, also through the normal operating channel of a standard gastroscope.

BRIEF DESCRIPTION OF THE DRAWINGS

Further characteristics and advantages of the present invention will appear clear from the description of the following non-limiting embodiment examples, with reference to the figures of the accompanying drawings, in which:

FIG. 1 is a side elevation schematic view, with a detail on an enlarged scale and in section of an intragastric balloon according to the invention;

FIGS. 2 and 3 show the intragastric balloon of FIG. 1 in use, during filling with a filling fluid and after filling, respectively;

FIGS. 4 and 5 show respective steps of the manufacturing method of the intragastric balloon of FIG. 1;

BEST MODE FOR CARRYING OUT THE INVENTION

Figure 6:
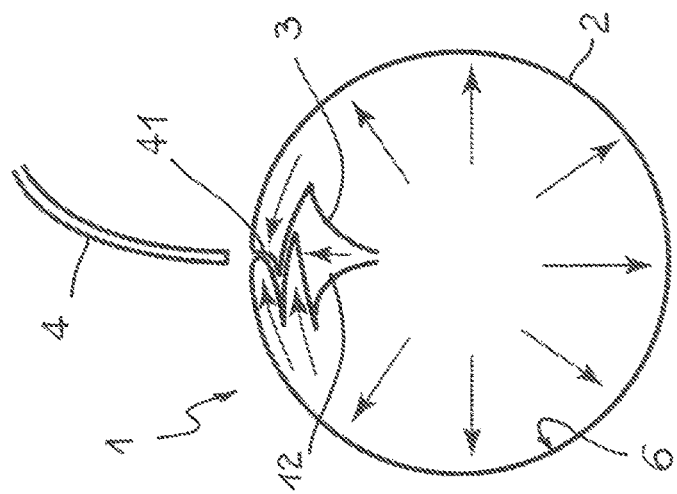
FIG. 6 is a side elevation schematic view of a variation of the intragastric balloon of the invention.

With reference to FIGS. 1-3, an intragastric balloon 1 extends along a longitudinal axis A and comprises a bag body 2 with an internal cavity and at least one valve 3 for feeding a filling fluid into said bag body 2.

FIGS. 1-3 also show, only schematically and partially, a probe 4 through which the filling fluid can be introduced into the balloon 1, as will be better clarified below.

The bag body 2 is made of an elastic material, for example a polymer material, namely elastomeric, such as latex, polyurethane, etc.

Preferably, the bag body 2 is made of a film having a thickness ranging between 0.1 and 200 micron.

The bag body 2 extends substantially along and around the axis A and is provided with an internal cavity 6 shaped to contain the filling fluid.

The bag body 2 can be expanded as a result of the introduction of an appropriate quantity of filling fluid passing from a deflated conformation (shown in FIG. 1) in which the bag body 2 is substantially flat, to an expanded conformation (shown in FIG. 3), in which the bag body 2 has a rounded shape (for example, substantially spheroidal).

The bag body 2 can have various shapes, both in the deflated conformation and in the expanded conformation.

In general, the bag body 2 has a substantially flat shape in the deflated conformation, being formed by a pair of substantially flat walls 7 facing each other and joined along a perimeter edge 8 of the bag body 2; and a three-dimensional and generically rounded shape in the expanded conformation.

In the example shown in FIG. 1, but not necessarily, the bag body 2 has an oblong substantially ogival shape along the axis A. It is understood that the bag body 2 can have a different shape, for example round, polygonal, etc.

The bag body 2 has a through access opening 10 communicating with the cavity 6 and positioned for example at a longitudinal end of the bag body 2 along the axis A.

The access opening 10 communicates with the valve 3, which is positioned entirely within the bag body 2 inside the cavity 6.

The valve 3 projects from an inner surface 11 of the bag body 2 into the cavity 6 and comprises a flexible and elastically deformable valve body 12, made of an elastic material (for example the same material as the bag body 2) and configured to selectively open/close the valve 3 by means of elastic deformation of the valve body 12.

In particular, the valve 3 consists solely of the valve body 12.

The valve body 12 is positioned inside the bag body 2 in the cavity 6 and is joined integral with the inner surface 11 of the bag body 2.

The valve body 12 extends along the axis A between a root end 13, joined to the inner surface 11, and a free end 14, axially opposite the root end 13. The valve body 12 is joined to the inner surface 11 by a loop-closed peripheral edge 15 positioned around the access opening 10.

The valve body 12 is internally hollow and has a through inner conduit 16 which crosses the valve body 12 and connects the access opening 10 to an end opening 17 of the valve 3, positioned at the free end 14 of the valve body 12. The conduit 16 is delimited by a side wall 18 of the valve body 12 extending substantially around the axis A.

The end opening 17 is delimited by a peripheral edge 19 and communicates with the inside of the bag body 2, i.e. with the cavity 6.

The side wall 18 of the valve body 12 has an inner surface 21, facing the conduit 16 which delimits the conduit 16, and an outer surface 22, opposite the inner surface 21 and facing the cavity 6 and the inner surface 11 of the bag body 2.

The side wall 18 of the valve body 12 is flexible and elastically deformable in a crosswise (radial) direction with respect to the conduit 16 to occlude the conduit 16.

The valve body 12 is shaped so as to elastically deform until it occludes the conduit 16 as a result of a pressure exerted on the outer surface 22 of the valve body 12 by the filling fluid contained in the cavity 6.

In particular, the valve body 12 has a shape such that the pressure exerted by the filling fluid on the outer surface 22 of the valve body 12 causes the squeezing of at least one elastic wall portion 23 of the conduit 16 and the consequent closing of the conduit 16.

The elastic wall portion 23 is squeezed so as to occlude the conduit 16 when the bag body 2, as a result of the introduction of the filling fluid, takes on the expanded conformation and contains a predetermined amount of filling fluid.

In other words, the valve body 12 and in particular the side wall thereof 18 are shaped so as to be squeezed crosswise (radially) with respect to the conduit 16 until they occlude the conduit 16 when there is a positive pressure difference between the outer surface 22 and the inner surface 21 of the valve body 12, namely when the pressure difference between the pressure exerted by the filling fluid on the outer surface 22 of the valve body 12, and the pressure inside the conduit 16 exceeds a predetermined threshold.

The valve body 12 can have various shapes, such that a pressure difference between the opposite surfaces 21, 22 (inner and outer) of the valve body 12 causes squeezing of the side wall 18, in particular at least of the elastic wall portion 23, and consequent closing of the conduit 16.

In the embodiment shown in FIGS. 1-3, the valve body 12 has an elongated shape along the axis A and tapers towards the free end 14 provided with the end opening 17.

In particular, the valve body 12 has a substantially lanceolate shape and comprises at least a cusp portion, tapering towards the free end 14.

Preferably, the valve body 12 has a length (measured along the axis A between the root end 13 and the free end 14) which is equal to at least half, or more preferably to at least three quarters, of the length of the bag body 2 (again measured along the axis A between opposite longitudinal ends of the bag body 2).

Preferably, but not necessarily, the valve body 12 has a narrowing 24 at the root end 13.

Advantageously, furthermore, the end opening 17 and/or the access opening 10 have a diameter (internal) smaller than the diameter (external) of the probe 4 used to introduce the filling fluid into the balloon 1 and preferably equal to or smaller than approximately 50% of the diameter (external) of the probe 4. In particular, the end opening 17 and/or the access opening 10 have a diameter smaller than approximately 1.5 mm and preferably smaller than approximately 1.2 mm.

Preferably, but not necessarily, the end opening 17 has a diameter smaller than the access opening 10. For example, the end opening 17 has a diameter smaller than or equal to approximately 1.0 mm or 0.8 mm; and the access opening 10 has a diameter smaller than or equal to approximately 1.2 mm.

In the example shown in FIGS. 1-3, the valve body is formed by two flaps 25 (only one of which is visible in FIGS. 1-3) which are flat and face each other, substantially plane and parallel (in the deflated conformation of the balloon) and joined along respective side edges.

Advantageously, the valve body 12 forms a monolithic piece together with the bag body 2.

The entire balloon 1 (bag body 2 and valve body 12) is preferably made of a film material with thickness ranging from 0.1 to 200 micron.

The balloon 1 of the invention, due to its shape and the thickness of the material with which it is made, can be wound, coiled and/or folded until it has a maximum external diameter smaller than 5 mm and even less.

In this way, the balloon 1 can be inserted in an operating channel of a standard gastroscope, with which the balloon 1 can then be implanted in the stomach of a patient.

Once inserted in the stomach of the patient, the balloon 1 (deflated) is filled with filling fluid by means of the probe 4 which also passes directly into the operating channel of the gastroscope. The doctor maintains the possibility of visually monitoring the operation, via the same gastroscope.

The filling fluid is a liquid for example, in particular water or saline solution (if necessary with the addition of a dye).

The probe 4 is inserted (FIG. 2) through the access opening 10 and the end opening 17; the probe 4 then crosses the valve 3 and penetrates into the cavity 6, where it releases the filling fluid. The end opening 17 and/or the access opening 10 are sized so that the respective peripheral edges 15, 19 adhere closely to the probe 4, preventing the outlet of the filling fluid and also preventing the probe 4 from accidentally sliding out.

The introduction of the filling fluid expands the bag body 2, which takes on the expanded conformation.

Once the filling has been completed (FIG. 3), the probe 4 is extracted from the valve 3 and from the balloon 1: the pressure exerted by the filling fluid on the outer surface 22 of the valve body 12 elastically deforms the side wall 18 of the valve body 12, in particular pushing the two flaps 25 against each other, until occluding the conduit 16 and closing the valve 3.

With reference also to FIGS. 4-5, the balloon 1 is advantageously made, according to the manufacturing method of the invention, as follows.

Firstly, a blank piece 30 is provided made of elastic material (i.e. the material selected for making the bag body 2 and the entire balloon 1), formed by two substantially plane film elements 31 which are welded together along respective side edges 32.

Each film element 31, as shown in FIG. 4, extends along a longitudinal axis B (which will then be parallel to or coinciding with the axis A of the balloon 1) and comprises a base portion 33, having the shape in plan view of a wall 7 of the bag body 2, and a projection 34, which projects longitudinally from the base portion 33 and has the shape in plan view of a flap 25 of the valve body 12. The base portion 33 and the projection 34 form a substantially flat monolithic piece and are joined by a groove 35.

Each film element 31 extends along the axis B between two axial opposite ends 36, 37, namely a free end of the base portion 33, opposite the projection 34 and the groove 35, and a tapered free end of the projection 34.

Clearly, the two film elements 31 can also be cut from the same film of material with a common edge portion (so that the two film elements 31 form one single piece).

In any case, the two film elements 31 are then positioned one over the other (if necessary folding them towards each other along the common edge portion) with the respective side edges 32 superimposed in contact with each other.

The side edges 32 of the two film elements 31 are then welded together, preferably by means of a high frequency welding process.

The two film elements 31 are welded together along the entire length of the side edges 32, except for two pairs of edge portions 38, 39 facing each other (schematically indicated by a broken line in FIG. 4) at the axial ends 36, 37; the edge portions 38, 39 are not welded and respectively define a service opening 40 (which will subsequently be closed) and the end opening 17 of the valve body 12 (which instead will remain open).

The grooves 35 are shaped and sized so that the side edges 32, once welded, are spaced from each other by a space defining the access opening 10.

The base portions 33 of the two film elements 31 thus form respective walls 7 of the bag body 2 of the balloon 1, whereas the projections 34 form respective flaps 25 of the valve body 12. The valve body 12 is on the outside of the bag body 2.

At this point, the blank piece 30 formed by the two film elements 31 welded together is turned inside out (FIG. 5) through the service opening 40, bringing the valve body 12 and the weldings made along the side edges 32 inside the bag body 2.

Lastly, the edge portions 38 facing each other are welded, thus closing the service opening 40.

The weldings remain inside the bag body 2, except along the edge portions 38.

Figure 7:
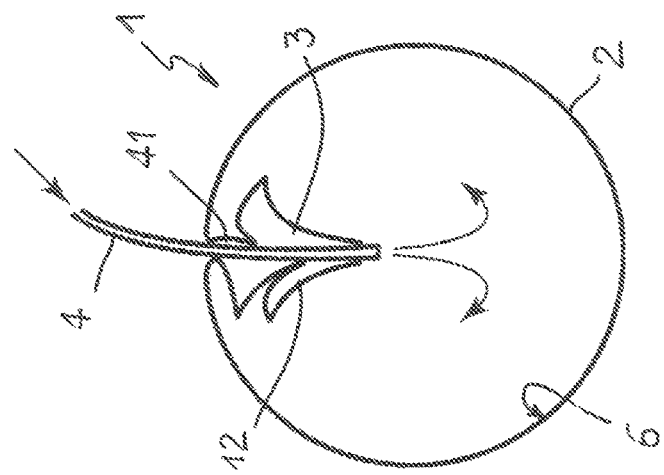
FIGS. 7 and 8 show the intragastric balloon of FIG. 6 in use, during filling with a filling fluid and after filling, respectively.
Figure 8:
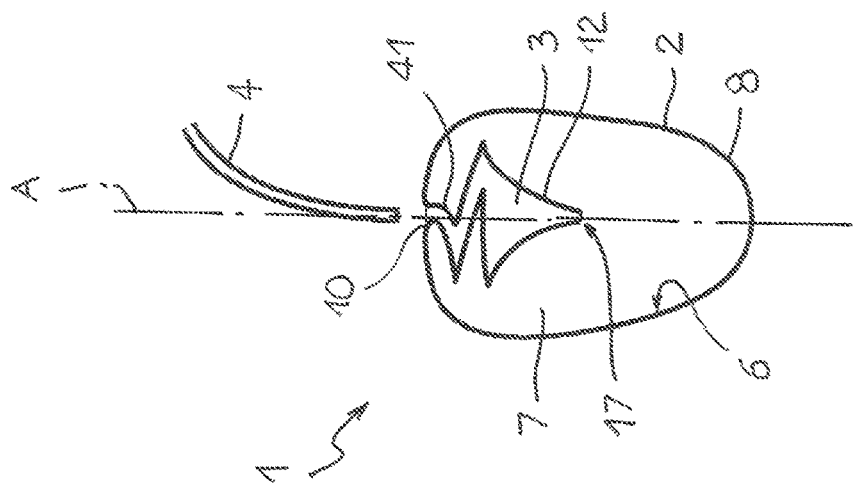

In the variation shown in FIGS. 6-8, in which the details similar or equal to those already described are indicated by the same numbers, the valve body 12 of the valve 3 is connected to the surface 11 of the bag body 2 by a flexible tubular strap 41, integral with the valve body 12 (and with the bag body 2) and in the same material as the valve body 12.

The strap 41 is hollow inside and communicates with the access opening 10 and with the internal conduit 16 of the valve body 12 to allow insertion of the probe 4. The strap 41 preferably has a cross section smaller than the cross section of the valve body 12 and, in non-deformed conditions, has a substantially zigzag or serpentine shape.

The strap 41 contributes to increasing the seal of the valve 3, acting as a further safety system able to prevent the outflow of filling fluid from the cavity 6, while allowing insertion of the probe 4 for filling of the balloon 1.

Figure 10:
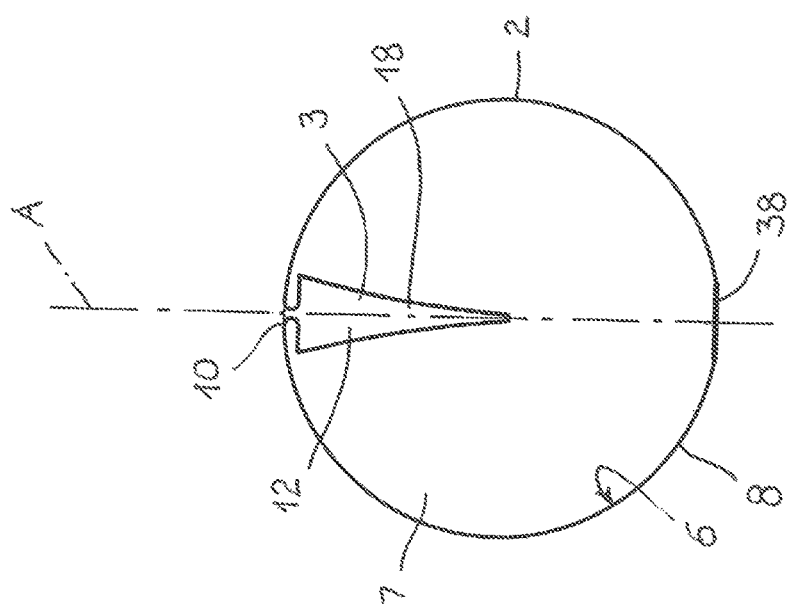
FIGS. 9 and 10 show another variation of the intragastric balloon of the invention, during manufacture and once finished, respectively.
Figure 9:
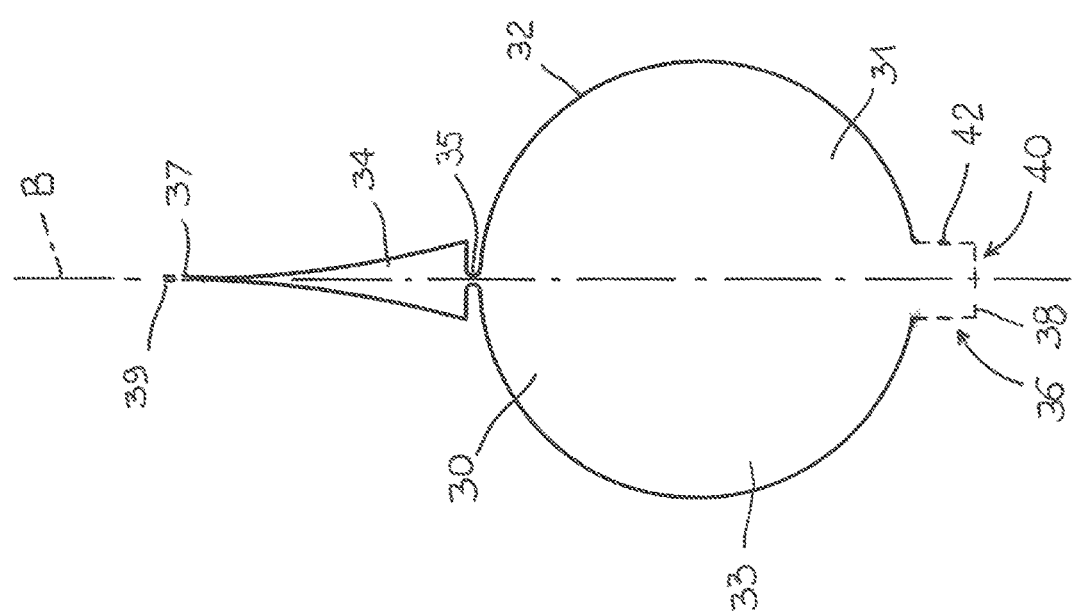

In the further variation shown in FIGS. 9-10, in which the details similar or equal to those already described are indicated by the same numbers, the blank piece 30 (FIG. 9) made of elastic material is still formed by two substantially plane and superimposed film elements 31, having respective base portions 33 and respective projections 34.

In this case, the base portion 33 of each film element 31 (and therefore the wall 7 of the bag body 2) has a substantially rounded shape in plan view, for example substantially circular.

Furthermore, the end 36 of the film element 31 (defining the free end of the base portion 33, opposite the projection 34) is provided with a tongue 42 protruding from the base portion 33 along the axis B and opposite the projection 34.

Also in this case, the two film elements 31 are superimposed on each other with the respective side edges 32 in contact with each other.

The side edges 32 of the two film elements 31 are therefore welded together, preferably by means of a high frequency welding process, along respective welding portions which extend substantially over the entire length of the side edges 32, except for two pairs of edge portions 38, 39 facing each other (schematically indicated by a broken line in FIG. 9) at the axial ends 36, 37.

The edge portions 38 extend in particular along the contour of the tongues 42.

The edge portions 38, 39 are not welded so as to respectively define the service opening 40 and the end opening 17 of the valve body 12.

The tongues 42 facilitate the subsequent turning inside out of the blank piece 30 formed of the two film elements 31 welded together through the service opening 40.

Also in this case, the valve body 12 and the weldings made along the side edges 32 are brought inside the bag body 2 and then the facing edge portions 38 are welded, thus closing the service opening 40 (FIG. 10).

Lastly, it is understood that further modifications and variations that do not depart from the scope of the attached claims can be made to the intragastric balloon and manufacturing method thereof described and illustrated here.

The invention claimed is:

1. An intragastric balloon (1), comprising
a bag body (2), provided with an internal cavity (6) shaped so as to contain a filling fluid, and
at least one valve (3) having a valve body (12) provided with a through inner conduit (16) for feeding the filling fluid into the cavity (6); the valve body (12) being flexible and elastically deformable, being made of an elastic material, the valve body (12) having a shape elongated along an axis (A) and tapering inwardly at a free end (14) provided with an end opening (17), and being positioned inside the bag body (2) and shaped so as to deform elastically until it occludes the conduit (16) following a pressure exerted on an outer surface (22) of the valve body (12) by the filling fluid contained in the cavity (6); characterized in that the valve body (12) is made integral in one piece with the bag body (2) and with the same material as the bag body (2), forming together with the bag body (2) a monolithic piece made of elastic material,
wherein the valve body (12) has a length, measured along the axis (A) between a root end (13) and the free end (14), which is equal to at least half of a length of the bag body (2), measured along the axis (A) between opposite longitudinal ends of the bag body (2),
wherein the valve body (12) has a shape such that the pressure exerted by the filling fluid on the outer surface (22) of the valve body (12) causes the squeezing of at least one elastic wall portion (23) of the conduit (16) and consequent closing of the conduit (16), and
wherein the valve body (12) has a substantially lanceolate shape and comprises at least a cusp portion, tapering toward the free end (14).

2. The intragastric balloon according to claim 1, wherein the bag body (2) is expandable as a result of the introduction of the filling fluid passing from a deflated conformation, in which the bag body (2) is substantially flat, to an expanded conformation, in which the bag body (2) has a rounded shape and contains at least a predetermined amount of the filling fluid such as to squeeze crosswise, acting on the outer surface (22) of the valve body (12), said elastic wall portion (23) of the conduit (16) and occlude the conduit (16).

3. The intragastric balloon according to claim 1, wherein the conduit (16) is delimited by a side wall (18) which is flexible and elastically deformable crosswise to the conduit (16) for occluding the conduit (16).

4. The intragastric balloon according to claim 1, wherein the bag body (2) has an access opening (10) communicating with an outside and delimited by a loop-closed peripheral edge (15); and the valve body (12) is joined to an inner surface (11) of the bag body (2) by said peripheral edge (15) and projects inside the cavity (6) between the root end (13), communicating with said access opening (10), and the free end (14), provided with an end opening (17) communicating with the cavity (6).

5. The intragastric balloon according to claim 4, wherein the valve body (12) has a narrowing (24) at the root portion (13).

6. The intragastric balloon according to claim 4, wherein the end opening (17) and/or the access opening (10) have a diameter smaller than approximately 1.5 mm and preferably smaller than approximately 1.2 mm.

7. The intragastric balloon according to claim 1, wherein the valve body (12) is formed by two flat flaps (25) facing each other, substantially planar and parallel and joined along respective side edges (32).

8. The intragastric balloon according to claim 1, wherein the monolithic piece formed of the bag body (2) and the valve body (12) is made of elastomeric material.

9. The intragastric balloon according to claim 1, wherein the valve body (12) is joined to the inner surface (11) of the bag body (2) by a flexible tubular strap (41), made integrally in one piece with the valve body (12) and of the same material as the valve body (12).

10. A method for manufacturing an intragastric balloon according to claim 1, comprising the steps of:
providing a pair of substantially flat film elements (31) made of elastic material, in particular elastomeric material, comprising respective base portions (33), defining respective walls (7) of the bag body (2), and respective projections (34), extending from the respective base portions (33) and defining respective flaps (25) of the valve body (12);
placing the two film elements (31) one upon the other with respective superimposed side edges (32) and welding together along said side edges (32) the two film elements (31) forming an elastic material blank piece (30), in which the base portions (33) of the film elements (31) form the bag body (2) and the projections (34) of the film elements (31) form the valve body (12);
leaving free of welding at least a pair of respective edge portions (38), facing each other, of the side edges (32) of the two film elements (31), thus leaving a service opening (40), free of welding, in the blank piece (30);
turning inside out, through the service opening (40), the blank piece (30) formed by the two film elements (31) welded together, bringing the valve body (12) inside the bag body (2);
welding together the edge portions (38) of the side edges (32) of the two film elements (31) and thus closing the service opening (40).

11. The method according to claim 10, wherein in the step of welding together the two film elements (31) forming the blank piece (30) the side edges (32) of the two film elements (31) are welded along the whole length of the side edges (32), except for two pairs of edge portions (38, 39) facing each other at respective opposite axial ends (36, 37) of the film elements (31) which are not welded and define said service opening (40) and the end opening (17) of the valve body (12) respectively.

12. The method according to claim 10, wherein the base portion (33) and the projection (34) of each film element (31) form a monolithic piece, obtained from a film of an elastic material, in particular an elastomeric material.

13. The method according to claim 10, wherein in the blank piece (30) the service opening (40) is substantially aligned with the projections (34) of the film elements (31).

14. The method according to claim 10, wherein the side edges (32) of the film elements (31) are welded by means of a high frequency welding process.

* * * * *